US010863961B2

(12) United States Patent
Ohashi

(10) Patent No.: US 10,863,961 B2
(45) Date of Patent: Dec. 15, 2020

(54) MEDICAL IMAGE PROCESSING APPARATUS AND X-RAY DIAGNOSIS APPARATUS

(71) Applicant: CANON MEDICAL SYSTEMS CORPORATION, Otawara-shi (JP)

(72) Inventor: Shumpei Ohashi, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 106 days.

(21) Appl. No.: 16/294,961

(22) Filed: Mar. 7, 2019

(65) Prior Publication Data
US 2019/0274651 A1  Sep. 12, 2019

(30) Foreign Application Priority Data

Mar. 7, 2018  (JP) .................................. 2018-041078
Mar. 5, 2019  (JP) .................................. 2019-039766

(51) Int. Cl.
A61B 6/00 (2006.01)
A61B 6/02 (2006.01)
G06T 7/00 (2017.01)

(52) U.S. Cl.
CPC .......... A61B 6/5205 (2013.01); A61B 6/4441 (2013.01); A61B 6/481 (2013.01); A61B 6/486 (2013.01); A61B 6/5217 (2013.01); A61B 6/02 (2013.01); A61B 6/463 (2013.01); A61B 6/504 (2013.01); A61B 6/5264 (2013.01); A61B 6/54 (2013.01); G06T 7/0012 (2013.01); G06T 2207/10116 (2013.01); G06T 2207/30004 (2013.01)

(58) Field of Classification Search
CPC ....... A61B 6/4441; A61B 6/481; A61B 6/504; A61B 6/487; A61B 6/542; A61B 6/5205; A61B 6/463; A61B 6/482; A61B 6/486; A61B 6/503; A61B 6/5288; A61B 6/5229; G06T 7/0012; G06T 2207/30104; G06T 7/174
See application file for complete search history.

(56) References Cited

U.S. PATENT DOCUMENTS

2003/0229285 A1  12/2003  Simpson et al.
2007/0195932 A1  8/2007  Nakaura et al.
(Continued)

FOREIGN PATENT DOCUMENTS

JP  2005-528949  9/2005
JP  2007-215925  8/2007
(Continued)

Primary Examiner — Don K Wong
(74) Attorney, Agent, or Firm — Oblon, McClelland, Maier & Neustadt, L.L.P.

(57) ABSTRACT

A medical image processing apparatus according to an embodiment includes processing circuitry configured: to sequentially acquire X-ray images; to set a unit number of frames used as a unit during image processing; and to sequentially generate images in each of which a pixel value of each pixel expresses either the largest pixel value or the smallest pixel value among corresponding pixels in X-ray images corresponding to the unit number of frames, on the basis of the X-ray images corresponding to the unit number of frames including each of new X-ray image that is sequentially acquired and at least one X-ray image acquired before the new X-ray image.

20 Claims, 9 Drawing Sheets

(56) References Cited

U.S. PATENT DOCUMENTS

2008/0262354 A1   10/2008  Yoshida et al.
2015/0374323 A1*  12/2015  Shiraishi ................ A61B 6/481
                                                         378/42

FOREIGN PATENT DOCUMENTS

| JP | 2010-279594 | 12/2010 |
| --- | --- | --- |
| JP | 2011-104055 | 6/2011 |
| JP | 4945605 B2 | 6/2012 |
| JP | 5323275 B2 | 10/2013 |

* cited by examiner

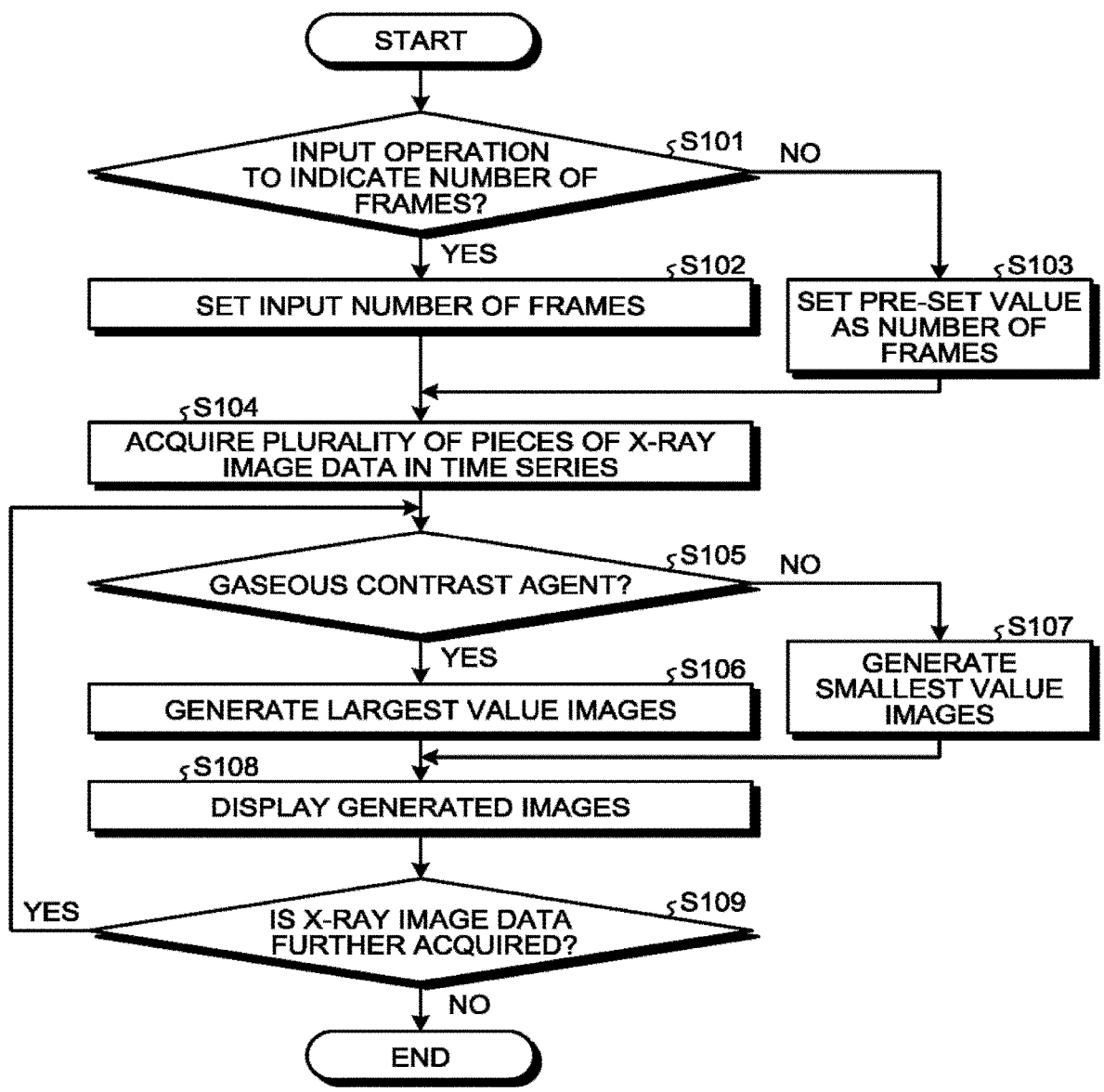

MEDICAL IMAGE PROCESSING APPARATUS AND X-RAY DIAGNOSIS APPARATUS

CROSS-REFERENCE TO RELATED APPLICATIONS

This application is based upon and claims the benefit of priority from Japanese Patent Application No. 2018-41078, filed on Mar. 7, 2018; and Japanese Patent Application No. 2019-39766, filed on Mar. 5, 2019, the entire contents of which are incorporated herein by reference.

FIELD

Embodiments described herein relate generally to a medical image processing apparatus and an X-ray diagnosis apparatus.

BACKGROUND

During medical examinations using an X-ray diagnosis apparatus, a contrast agent may be used in some situations to acquire X-ray images rendering blood vessels. For example, by radiating X-rays onto a subject (e.g. patient) who has a contrast agent injected in blood vessels, the X-ray diagnosis apparatus acquires X-ray images rendering the blood vessels of subject. However, for some subjects, there may be a restriction about the amount or the type of the contrast agent to be used. For example, when the subject has a kidney disease or is allergic to iodine (I), using a contrast agent of which the main component is iodine is restricted. In that situation, for example, X-ray images are acquired by reducing the amount of the contrast agent to be used or by changing the type of the contrast agent.

BRIEF DESCRIPTION OF THE DRAWINGS

FIG. 4 is a flowchart for explaining a flow in a series of processes performed by a medical image processing apparatus according to the first embodiment;

DETAILED DESCRIPTION

Exemplary embodiments of a medical image processing apparatus, an X-ray diagnosis apparatus, and a medical image processing computer program will be explained below in detail, with reference to the accompanying drawings.

To begin with, a first embodiment will be explained. In the first embodiment, a medical information processing system including a medical image processing apparatus and an X-ray diagnosis apparatus will be explained as an example.

Figure 1:
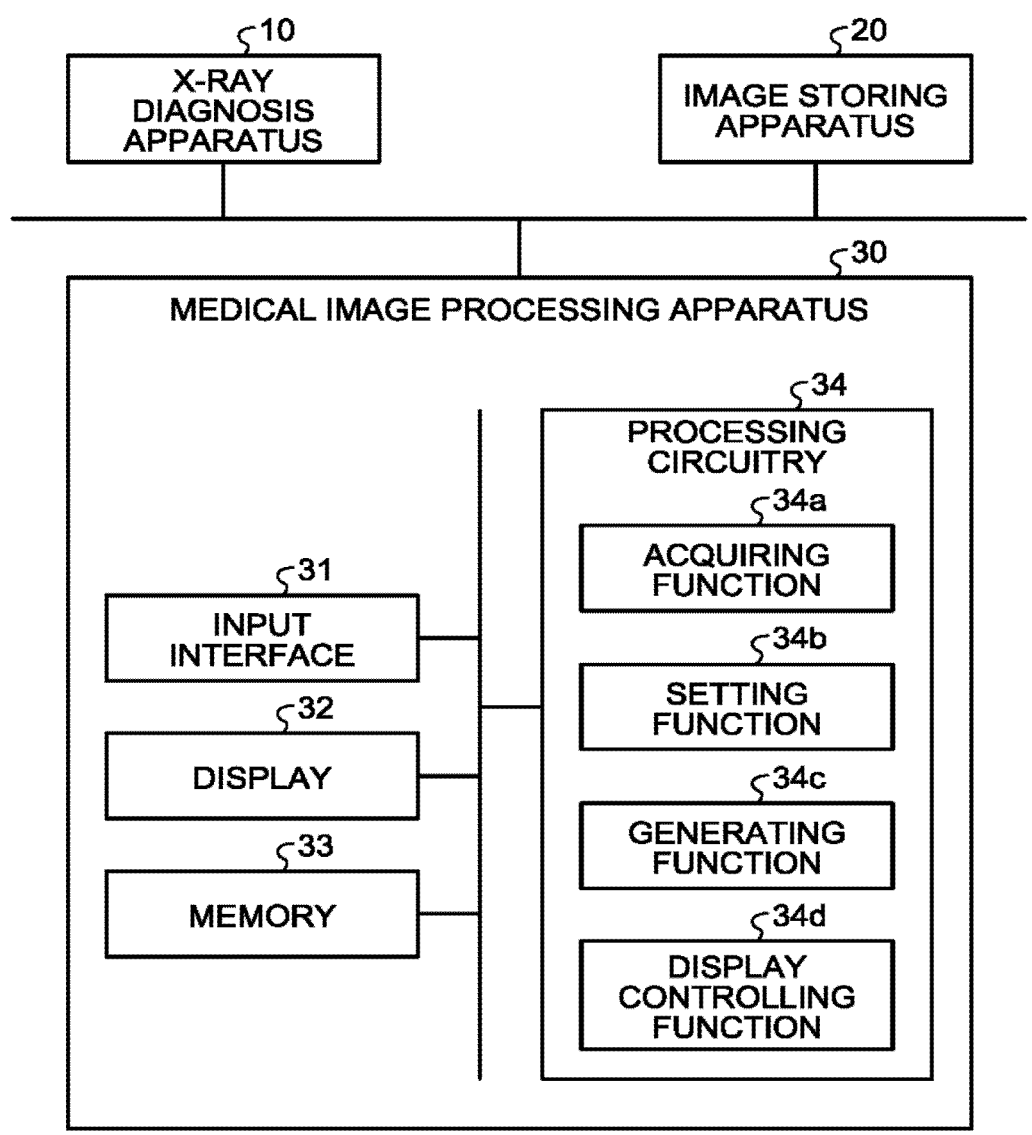
FIG. 1 is a block diagram illustrating an exemplary configuration of a medical information processing system according to a first embodiment.

As illustrated in FIG. 1, a medical information processing system 1 according to the first embodiment includes an X-ray diagnosis apparatus 10, an image storing apparatus 20, and a medical image processing apparatus 30. FIG. 1 is a block diagram illustrating an exemplary configuration of the medical information processing system 1 according to the first embodiment. As illustrated in FIG. 1, the X-ray diagnosis apparatus 10, the image storing apparatus 20, and the medical image processing apparatus 30 are connected to one another via a network.

The X-ray diagnosis apparatus 10 is configured to acquire one or more X-ray images from a subject P. X-ray images processed as data may also be referred to as X-ray image data. For example, the X-ray diagnosis apparatus 10 acquires a plurality of pieces of X-ray image data in a time series from the subject P and transmits the acquired plurality of pieces of X-ray image data to the image storing apparatus 20 and to the medical image processing apparatus 30. A configuration of the X-ray diagnosis apparatus 10 will be explained later.

The image storing apparatus 20 is configured to store therein a plurality of pieces of X-ray image data acquired by the X-ray diagnosis apparatus 10. For example, the image storing apparatus 20 is realized by using a computer device such as a server. In the present embodiment, the image storing apparatus 20 acquires the plurality of pieces of X-ray image data from the X-ray diagnosis apparatus 10 via the network and stores the acquired plurality of pieces of X-ray image data into a memory provided either inside or outside of the apparatus.

The medical image processing apparatus 30 is configured to acquire a plurality of pieces of X-ray image data in a time series via a network and to perform various types of processes by using the acquired plurality of pieces of X-ray image data. For example, the medical image processing apparatus 30 is realized by using a computer device such as a workstation. In the present embodiment, the medical image processing apparatus 30 acquires the plurality of pieces of X-ray image data in the time series acquired by the X-ray diagnosis apparatus 10. Further, the medical image processing apparatus 30 performs image processing on the acquired plurality of pieces of X-ray image data. The image processing performed by the medical image processing apparatus 30 will be explained later.

As illustrated in FIG. 1, the medical image processing apparatus 30 includes an input interface 31, a display 32, a memory 33, and processing circuitry 34.

The input interface 31 is realized by using a trackball, a switch, a button, a mouse, and/or a keyboard used for inputting various types of instructions and various types of settings, a touchpad used for performing an input operation by touching an operation surface thereof, a touch screen in which a display screen and a touch pad are integrally formed, a contactless input circuit using an optical sensor, an audio input circuit, and/or the like. The input interface 31 is configured to convert an input operation received from an operator into an electrical signal and to output the electrical signal to the processing circuitry 34. The input interface 31 does not necessarily have to include one or more physical operation component parts such as a mouse and a keyboard.

For example, possible examples of the input interface 31 include electrical signal processing circuitry configured to receive an electrical signal corresponding to an input operation from an external input device provided separately from the medical image processing apparatus 30 and to output the electrical signal to the processing circuitry 34.

The display 32 is configured to display various types of information. For example, the display 32 displays a Graphical User Interface (GUI) used for receiving an instruction from the operator and various types of image data. For example, the display 32 may be a liquid crystal display or a Cathode Ray Tube (CRT) display.

The memory 33 is realized by using, for example, a semiconductor memory element such as a Random Access Memory (RAM), a flash memory, or the like, or a hard disk, an optical disk, or the like. For example, the memory 33 is configured to store therein the plurality of pieces of X-ray image data in the time series acquired from the X-ray diagnosis apparatus 10. Further, for example, the memory 33 stores therein one or more computer programs (hereinafter, "programs") used by circuitry included in the medical image processing apparatus 30 for realizing the functions thereof.

The processing circuitry 34 is configured to control operations of the entirety of the medical image processing apparatus 30 by executing an acquiring function 34a, a setting function 34b, a generating function 34c, and a display controlling function 34d.

For example, the processing circuitry 34 is configured to acquire the plurality of pieces of X-ray image data in the time series from the X-ray diagnosis apparatus 10, by reading and executing a program corresponding to the acquiring function 34a from the memory 33. Further, for example, the processing circuitry 34 is configured to set the number of frames used as a unit during image processing that is performed for each of the groups made up of X-ray images in two or more frames, by reading and executing a program corresponding to the setting function 34b from the memory 33. Further, for example, the processing circuitry 34 is configured to generate an image in which the pixel value of each of the pixels expresses either the largest pixel value or the smallest pixel value among the corresponding pixels in the pieces of X-ray image data corresponding to the set number of frames, for each of the groups made up of X-ray images that correspond to the number of frames set by the setting function 34b and are among the plurality of pieces of X-ray image data in the time series, by reading and executing a program corresponding to the generating function 34c from the memory 33.

In the medical image processing apparatus 30 illustrated in FIG. 1, processing functions are stored in the memory 33 in the form of computer-executable programs. The processing circuitry 34 is a processor configured to realize the functions corresponding to the programs by reading and executing the programs from the memory 33. In other words, the processing circuitry 34 that has read the programs has the functions corresponding to the read programs. With reference to FIG. 1, the example was explained in which the single processing circuit realizes the acquiring function 34a, the setting function 34b, the generating function 34c, and the display controlling function 34d. However, another arrangement is also acceptable in which the processing circuitry 34 is structured by combining together a plurality of independent processors, so that the functions are realized as a result of the processors executing the programs.

Figure 2:
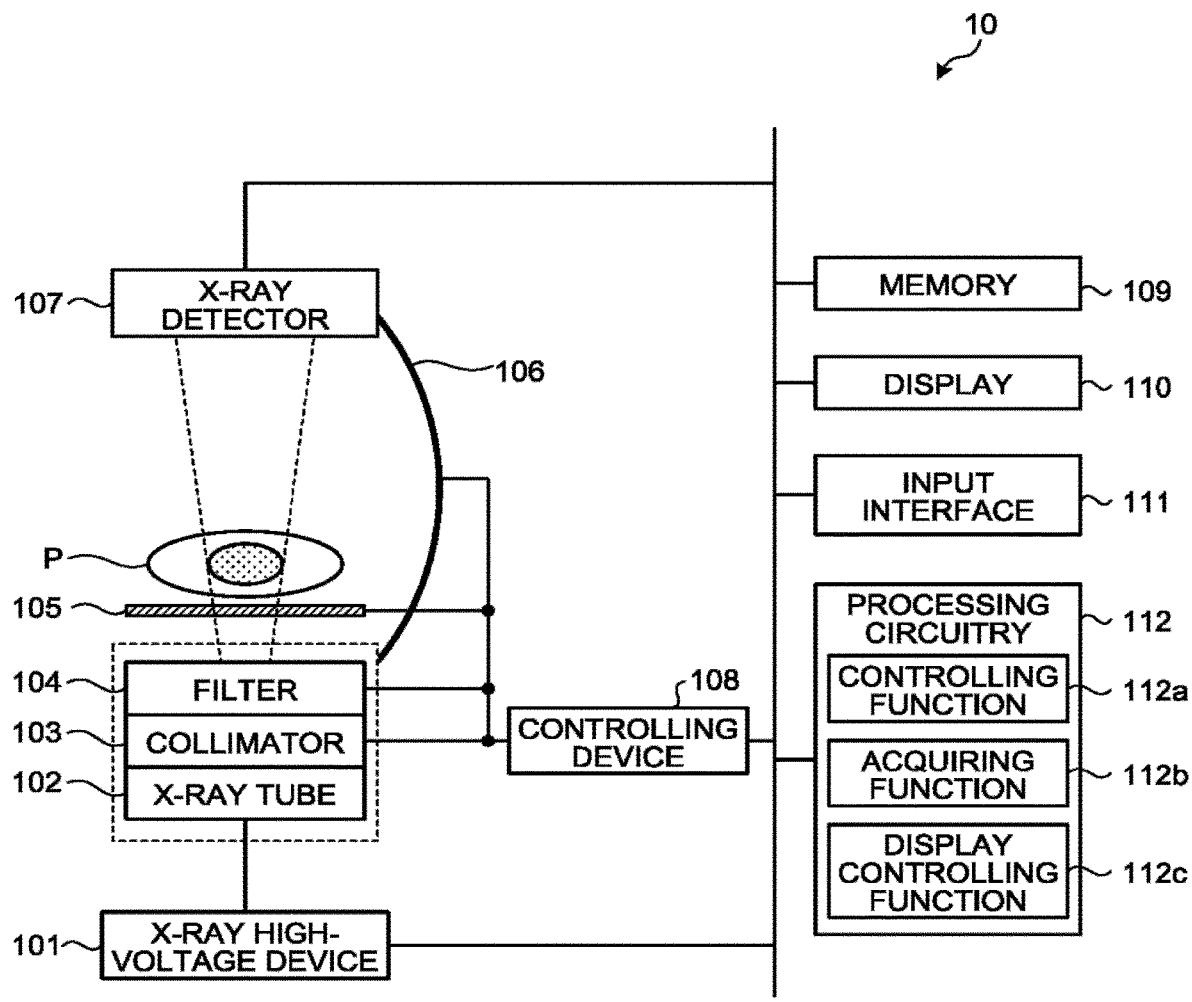
FIG. 2 is a block diagram illustrating an exemplary configuration of an X-ray diagnosis apparatus according to the first embodiment.

Next, the X-ray diagnosis apparatus 10 configured to acquire the plurality of pieces of X-ray image data in the time series will be explained with reference to FIG. 2. FIG. 2 is a block diagram illustrating an exemplary configuration of the X-ray diagnosis apparatus 10 according to the first embodiment. As illustrated in FIG. 2, the X-ray diagnosis apparatus 10 includes an X-ray high-voltage device 101, an X-ray tube 102, a collimator 103, a filter 104, a tabletop 105, a C-arm 106, an X-ray detector 107, a controlling device 106, a memory 109, a display 110, an input interface 111, and processing circuitry 112.

The X-ray high-voltage device 101 is configured to supply high voltage to the X-ray tube 102 under control of the processing circuitry 112. For example, the X-ray high-voltage device 101 includes: a high-voltage generating device that includes electric circuitry such as a transformer, a rectifier, and the like and is configured to generate the high voltage to be applied to the X-ray tube 102; and an X-ray controlling device configured to control the output voltage in accordance with the X-rays to be radiated by the X-ray tube 102. In this situation, the high-voltage generating device may be of a transformer type or an inverter type.

The X-ray tube 102 is a vacuum tube including a negative pole (a filament) configured to generate thermo electrons and a positive pole (a target) configured to generate the X-rays in response to collisions of the thermo electrons. The X-ray tube 102 is configured to generate the X-rays by emitting the thermos electrons from the negative pole toward the positive pole, by using the high voltage supplied thereto from the X-ray high-voltage device 101.

The collimator (which may also be referred to as an X-ray limiting device) 103 includes, for example, four slidable limiting blades. By sliding the limiting blades, the collimator 103 is configured to narrow down the X-rays generated by the X-ray tube 102 and to arrange the X-rays to be radiated onto the subject P. In this situation, the limiting blades are date-like members configured by using lead or the like and are disposed in the vicinity of an X-ray radiation opening of the X-ray tube 102 for the purpose of adjusting the radiation range of the X-rays.

The filter 104 is configured to reduce soft X-ray components that are easily absorbed by the subject P and to reduce high-energy components that may degrade the contrast of X-ray image data, by changing the quality of passing X-rays with the material and/or the thickness thereof, for the purpose of reducing the radiation exposure amount for the subject P and improving the quality of the X-ray image data. Further, the filter 104 is configured to attenuate the X-rays so that the X-rays radiated from the X-ray tube 102 onto the subject P have a distribution determined in advance, by changing the radiation dose and the radiation range of the X-rays with the material, the thickness, and/or the position thereof.

The tabletop 105 is a bed on which the subject P is placed and is arranged over a couch (not illustrated). The subject P is not included in the X-ray diagnosis apparatus 10.

The C-arm 106 is configured to hold the X-ray tube 102, the collimator 103, and the filter 104 so as to oppose the X-ray detector 107, while the subject P is interposed therebetween. Although FIG. 2 illustrates an example in which the X-ray diagnosis apparatus 10 is of a single-plane type, possible embodiments are not limited to this example. The X-ray diagnosis apparatus 10 may be of a bi-plane type.

The X-ray detector 107 is, for example, an X-ray Flat Panel Detector (FPD) including detecting elements arranged in a matrix formation. The X-ray detector 107 is configured to detect X-rays that were radiated from the X-ray tube 102 and have passed through the subject P and to output a detection signal corresponding to a detected X-ray amount to the processing circuitry 112. In this situation, the X-ray detector 107 may be an indirect-conversion type detector including a grid, a scintillator array, and an optical sensor array or may be a direct-conversion type detector including a semiconductor element configured to convert incident X-rays into an electrical signal.

The controlling device 108 includes: a driving mechanism structured with a motor and an actuator or the like; and circuitry configured to control the driving mechanism. Under control of the processing circuitry 112, the controlling device 108 is configured to control operations of the collimator 103, the filter 104, the tabletop 105, the C-arm 106, and the like. For example, the controlling device 108 is configured to control the radiation range of the X-rays to be radiated onto the subject P, by adjusting the opening degree of the limiting blades of the collimator 103. Further, the controlling device 108 is configured to control the distribution of the radiation dose of the X-rays radiated onto the subject P by adjusting the position of the filter 104. Further, for example, the controlling device 108 is configured to rotate and move the C-arm 106 and to move the tabletop 105.

The memory 109 is, for example, realized by using a semiconductor memory element such as a R a flash memory, or the like, or a hard disk, an optical disk, or the like. For example, the memory 109 is configured to receive and store therein the X-ray image data acquired by the processing circuitry 112. Further, the memory 109 is configured to store therein programs corresponding to various types of functions that are read and executed by the processing circuitry 112.

The display 110 is configured to display various types of information. For example, the display 110 is configured to display a GUI used for receiving instructions from an operator and various types of X-ray images. For example, the display 110 may be a liquid crystal display or a CRT display.

The input interface 111 is realized by using a trackball, a switch, a button, a mouse, and/or a keyboard used for inputting various types of instructions and various types of settings, a touchpad used for performing an input operation by touching an operation surface thereof, a touch screen in which a display screen and a touch pad are integrally formed, a contactless input circuit using an optical sensor, an audio input circuit, and/or the like. The input interface 111 is configured to convert an input operation received from an operator into an electrical signal and to output the electrical signal to the processing circuitry 112. The input interface 111 does not necessarily have to include one or more physical operation component parts such as a mouse and a keyboard. For example, possible examples of the input interface 111 include electrical signal processing circuitry configured to receive an electrical signal corresponding to an input operation from an external input device provided separately from the X-ray diagnosis apparatus 10 and to output the electrical signal to the processing circuitry 112.

The processing circuitry 112 is configured to control operations of the entirety of the X-ray diagnosis apparatus 10 by executing a controlling function 112a, an acquiring function 112b, and a display controlling function 112c. For example, the processing circuitry 112 is configured to control various types of functions of the processing circuitry 112 on the basis of the input operations received from the operator via the input interface 111, by reading and executing a program corresponding to the controlling function 112a from the memory 109.

Further, the processing circuitry 112 is configured to acquire the X-ray image data, by reading and executing a program corresponding to the acquiring function 112b from the memory 109. For example, the acquiring function 112b is configured to control the radiation dose and to turn on and off the X-rays radiated onto the subject P, by controlling the X-ray high-voltage device 101 so as to adjust the voltage supplied to the X-ray tube 102. Further, the acquiring function 112b is configured to control the radiation range of the X-rays radiated onto the subject. P, by controlling the controlling device 108 so as to adjust the opening degree of the limiting blades included in the collimator 103. Further, the acquiring function 112b is configured to control the distribution of the radiation dose of the X-rays by controlling the controlling device 108 so as to adjust the position of the filter 104. Further, the acquiring function 112b is configured to control the rotation and the moving of the C-arm 106 as well as the moving of the tabletop 105 and the like, by controlling the controlling device 108. Further, the acquiring function 112b is configured to generate the X-ray image data on the basis of the detection signal received from the X-ray detector 107 and to store the generated X-ray image data into the memory 109. In this situation, the acquiring function 112b may also perform various types of image processing on the X-ray image data stored in the memory 109. For example, the acquiring function 112b may perform a noise reducing process, a scattered ray correcting process, and/or the like on the X-ray image data, by using image processing filter.

Further, the processing circuitry 112 is configured to cause the display 110 to display the X-ray image data acquired by the acquiring function 112b, by reading and executing a program corresponding to the display controlling function 112c from the memory 109. Further, the display controlling function 112c is configured to cause the display 110 to display the GUI used for receiving instructions from the operator.

In the X-ray diagnosis apparatus 10 illustrated in FIG. 2, processing functions are stored in the memory 109 in the form of computer-executable programs. The processing circuitry 112 is a processor configured to realize the functions corresponding to the programs, by reading and executing the programs from the memory 109. In other words, the processing circuitry 112 that has read the programs has the functions corresponding to the read programs. With reference to FIG. 2, the example was explained in which the single processing circuit (i.e., the processing circuitry 112) realizes the controlling function 112a, the acquiring function 112b, and the display controlling function 112c. However, another arrangement is also acceptable in which the processing circuitry 112 is structured by combining together a plurality of independent processors, so that the functions are realized as a result of the processors executing the programs.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SOLD], a Complex Programmable Logic Device [COLD], or a Field Programmable Gate Array [FPGA]). One or more processors realize the functions by reading and executing the programs saved in either the memory 33 or the memory 109.

In this situation, the processors in the present embodiment do not each necessarily have to be structured as a single circuit. It is also acceptable to structure one processor by combining together a plurality of independent circuits so as to realize the functions thereof. Further, with reference to FIGS. 1 and 2, the examples were explained in which the single memory (the memory 33 and the memory 109) stores therein the programs corresponding to the processing functions. However, another arrangement is also acceptable in which a plurality of memories 33 are provided in a distributed manner, so that the processing circuitry 34 reads a corresponding program from each of the individual memories 33. Similarly, yet another arrangement is also acceptable in which a plurality of memories 109 are provided in a distributed manner, so that the processing circuitry 112 reads a corresponding program from each of the individual memories 109. Further, instead of saving the programs in the memory 33 and the memory 109, another arrangement is also acceptable in which the programs are directly incorporated in the circuits of the one or more processors. In that situation, the one or more processors realize the functions thereof by reading and executing the programs incorporated in the circuits thereof.

The medical information processing system 1 including the medical image processing apparatus 30 and the X-ray diagnosis apparatus 10 has thus been explained. The medical image processing apparatus 30 in the medical information processing system 1 structured as described above is configured to improve visibility of the X-ray images with the processes performed by the processing circuitry 34 explained in detail below. In the following sections, processes performed by the medical image processing apparatus 30 according to the first embodiment will be explained in detail.

First, the setting function 34b sets the number of frames used as a unit during image processing. For example, by receiving an input operation indicating the number of frames via the input interface 31, the setting function 34b sets the number of frames. In the following sections, an example will be explained in which "3 frames" is set as the number of frames used as a unit during the image processing.

Subsequently, the acquiring function 112b included in the X-ray diagnosis apparatus 10 acquires a plurality of pieces of X-ray image data in a time series. For example, the acquiring function 112b at first causes X-rays in a pulse form to be radiated onto the subject P from the X-ray tube 102. At that time, the X-ray detector 107 detects X-rays that have passed through the heart of the subject P and outputs a detection signal corresponding to the detected X-ray amount to the processing circuitry 112. After that, the acquiring function 112b generates X-ray image data on the basis of the detection signal received from the X-ray detector 107 and outputs the generated X-ray image data to the medical image processing apparatus 30. Further, the acquiring function 112b generates a piece of X-ray image data every time X-rays in a pulse form are radiated and sequentially outputs the generated pieces of X-ray image data to the medical image processing apparatus 30.

Figure 3A:
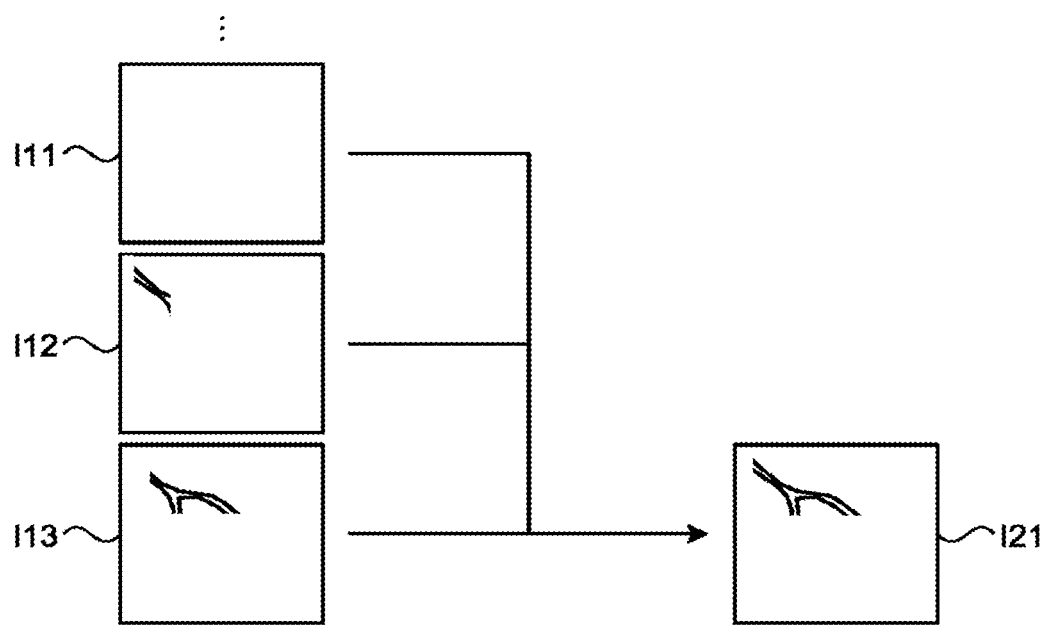
FIG. 3A is a drawing illustrating an example of image processing according to the first embodiment.

Subsequently, the acquiring function 34a acquires the plurality of pieces of X-ray image data in the time series. For example, the acquiring function 34a sequentially acquires the pieces of X-ray image data acquired by the acquiring function 112b and stores the acquired pieces of X-ray image data into the memory 33. For example, when the acquiring function 112b acquires a piece of X-ray image data I11 illustrated in FIG. 3A, the acquiring function 34a acquires and stores, into the memory 33, the piece of X-ray image data I11. After that, when the acquiring function 112b acquires another piece of X-ray image data I12, acquiring function 34a acquires and stores, into the memory 33, the piece of X-ray image data I12. After that, when the acquiring function 112b acquires yet another piece of X-ray image data I13, the acquiring function 34a acquires and stores, into the memory 33, the piece of X-ray image data I13. FIG. 3A is a drawing illustrating the example of the image processing according to the first embodiment.

In FIG. 3A, the piece of X-ray image data I11 X-ray image data in which the subject P is rendered while having no contrast agent injected in blood vessels. For example, the piece of X-ray image data I11 is X-ray image data acquired before a contrast agent is injected into the subject P.

Further, in FIG. 3A, the pieces of X-ray image data I12 and I13 are each X-ray image data in which the subject P is rendered while having the contrast agent injected in the blood vessels. For example, the pieces of X-ray image data I12 and I12 are each X-ray image data acquired by injecting the contrast agent in the radiation range of the X-rays or acquired after the contrast agent injected on the outside of the radiation range of the X-rays flows into the radiation range of the X-rays. The injection of the contrast agent may be performed by an injector (not illustrated) or may be performed by an operator.

In this situation, various types of contrast agents include: positive contrast agents each having an X-ray attenuation coefficient larger than those of peripheral tissues of the subject P; and negative contrast agents each having an X-ray attenuation coefficient smaller than those of peripheral tissues of the subject P. For example, the positive contrast agents are contrast agents of which the main component is iodine, barium sulfate, or the like. The negative contrast agents are, for example, gaseous contrast agents using carbon dioxide, oxygen, nitrogen, air, or the like. In the following sections, an example will be explained in which the contrast agent is carbon dioxide. As indicated by the pieces of X-ray image data I12 and I13 in FIG. 3A, the carbon dioxide injected in the blood vessels is rendered with pixel values larger (appear brighter) than the pixel values with which peripheral tissues are rendered. Further, the carbon dioxide injected in the blood vessels flows in the downstream direction along with the blood flow.

Subsequently, for each of the groups made up of pieces of X-ray image data that correspond to the number of frames "3 frames" set by the setting function 34b and are among the plurality of pieces of X-ray image data acquired by the acquiring function 34a, the generating function 34c generates a piece of image data in which the pixel value of each of the pixels expresses either the largest pixel value or the smallest pixel value among the corresponding pixels in the pieces of X-ray image data in the "3 frames". In this situation, the corresponding pixels may be, for example, pixels that are in mutually the same position (at mutually the same coordinates) in the pieces of X-ray image data. For example, the generating function 34c generates a piece of image data in which the pixel value of each of the pixels expresses either the largest pixel value or the smallest pixel value among the corresponding pixels in the pieces of X-ray image data I11, I12 and I13.

In the following sections, a piece of image data in which the pixel value of each of the pixels expresses the largest pixel values among the corresponding pixels in a plurality of pieces of X-ray image data will be referred to as a largest value image. Further, in the following sections, a piece of image data in which the pixel value of each of the pixels expresses the smallest pixel values among the corresponding pixels in a plurality of pieces of X-ray image data will be referred to as a smallest value image. The generating function 34c may generate both the largest value images and the smallest value images or may generate one selected from between the largest value images and the smallest value images.

For example, the generating function 34c generates one selected from between the largest value images and the smallest value images in accordance with the type of the contrast agent being used. In one example, when the contrast agent is carbon dioxide, the generating function 34c generates the largest value images. In this situation, the generating function 34c may acquire the type of the contrast agent being used by receiving an input operation from the operator or may acquire the type of the contrast agent being used from image taking conditions set for the subject P. Further, when the contrast agent is injected by using an injector, the generating function 34c may acquire the type of the contrast agent being used, from contrast enhancement conditions set with the injector.

For example, as illustrated in FIG. 3A, the generating function 34c generates a largest value image I21 in which the pixel value of each of the pixels expresses the largest pixel value among the corresponding pixels in the pieces of X-ray image data I11, I12, and I13. In this situation, because the carbon dioxide is rendered with pixel values larger than the pixel values with which the peripheral tissues are rendered, the carbon dioxide rendered in at least one of the pieces of X-ray image data I11, I12, and I13 is also rendered in the largest value image I21.

Carbon dioxide in a blood vessel may be separated at the time of being injected or while flowing through the blood vessel and may not be in the form of a single bubble. In that situation, in the pieces of X-ray image data I12 and I13, the blood vessel, which is supposed to be continuous, may be rendered as being divided in sections. In this situation, by generating the largest value image I21, the generating function 34c is able to render the blood vessel as being continuous and to thus improve the visibility. Further, depending on how the carbon dioxide spreads in the blood vessel, the contrast of the carbon dioxide to the peripheral tissues may be low in the X-ray image data, in some situations. Even in those situations, by generating the largest value image I21, the generating function 34c is able to emphasize the contrast of the carbon dioxide to the peripheral tissues and to thus improve the visibility.

The display controlling function 34d causes the display 32 to display the largest value image I21 generated by the generating function 34c. Further, the memory 33 stores therein the largest value image I21 generated by the generating function 34c. Alternatively, the generating function 34c may output the generated largest value image I21 to the image storing apparatus 20. In that situation, the image storing apparatus 20 stores therein the largest value image I21 generated by the generating function 34c. In one example, after generating the largest value image I21, the generating function 34c may delete the piece of X-ray image data I11 stored in the memory 33.

Figure 3B:
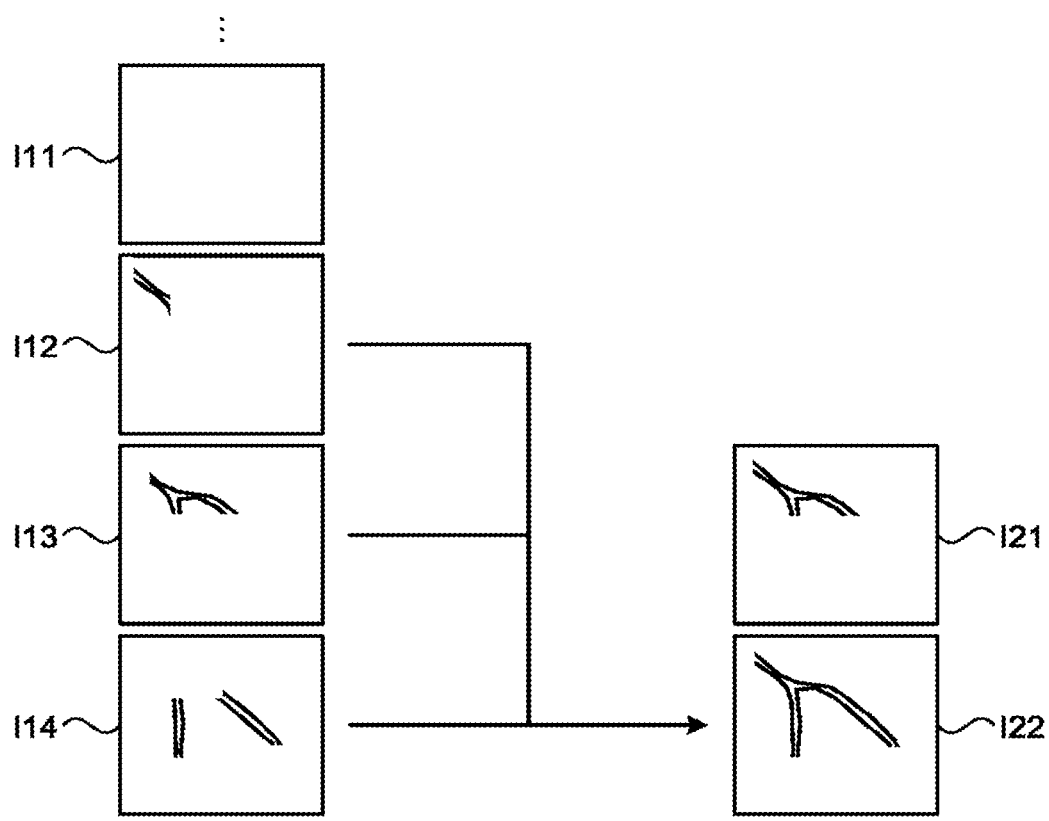
FIG. 3B is a drawing illustrating another example of the image processing according to the first embodiment.

After that, when the acquiring function 112b further acquires another piece of X-ray image data I14 illustrated in FIG. 3E, the acquiring function 34a acquires and stores, into the memory 33, the piece of X-ray image data I14. FIG. 3B is a drawing illustrating another example of the image processing according to the first embodiment. In FIG. 3B, the piece of X-ray image data I14 is X-ray image data in which the subject P is rendered while having the contrast agent injected in the blood vessels.

Subsequently, the generating function 34c generates a largest value image for each of the groups made up of pieces of X-ray image data that correspond to the number of frames "3 frames" set by the setting function 34b and are among the plurality of pieces of X-ray image data acquired by the acquiring function 34a. For example, as illustrated in FIG. 3B, the generating function 34c generates a largest value image I22 with respect to the pieces of X-ray image data in the "3 frames" including the new piece of X-ray image data I14 and the pieces of X-ray image data I12 and I13 acquired immediately before the piece of X-ray image data I14.

After that, the display controlling function 34d causes the display 32 to display the largest value image I22 generated by the generating function 34c. For example, the display controlling function 34d switches the display of the largest value image I21 that has been displayed on the display 32 into display of the largest value image I22. In this situation, as illustrated in FIG. 3E, when compared with the largest value image I21, the largest value image I22 renders the carbon dioxide that has diffused farther downstream. Accordingly, by having the largest value images I21 and I22 displayed, the operator is able to visually recognize not only the shapes of the blood vessels, but also the manner in which the contrast agent diffuses in the blood vessels.

Further, the memory 33 stores therein the largest value image I22 generated by the generating function 34c. Alternatively, the generating function 34c may output the generated largest value image I22 to the image storing apparatus 20. In that situation, the image storing apparatus 20 stores therein the largest value image I22 generated by the generating function 34c. After generating the largest value image I22, the generating function 34c may delete the piece of X-ray image data I12 stored in the memory 33.

Figure 3C:
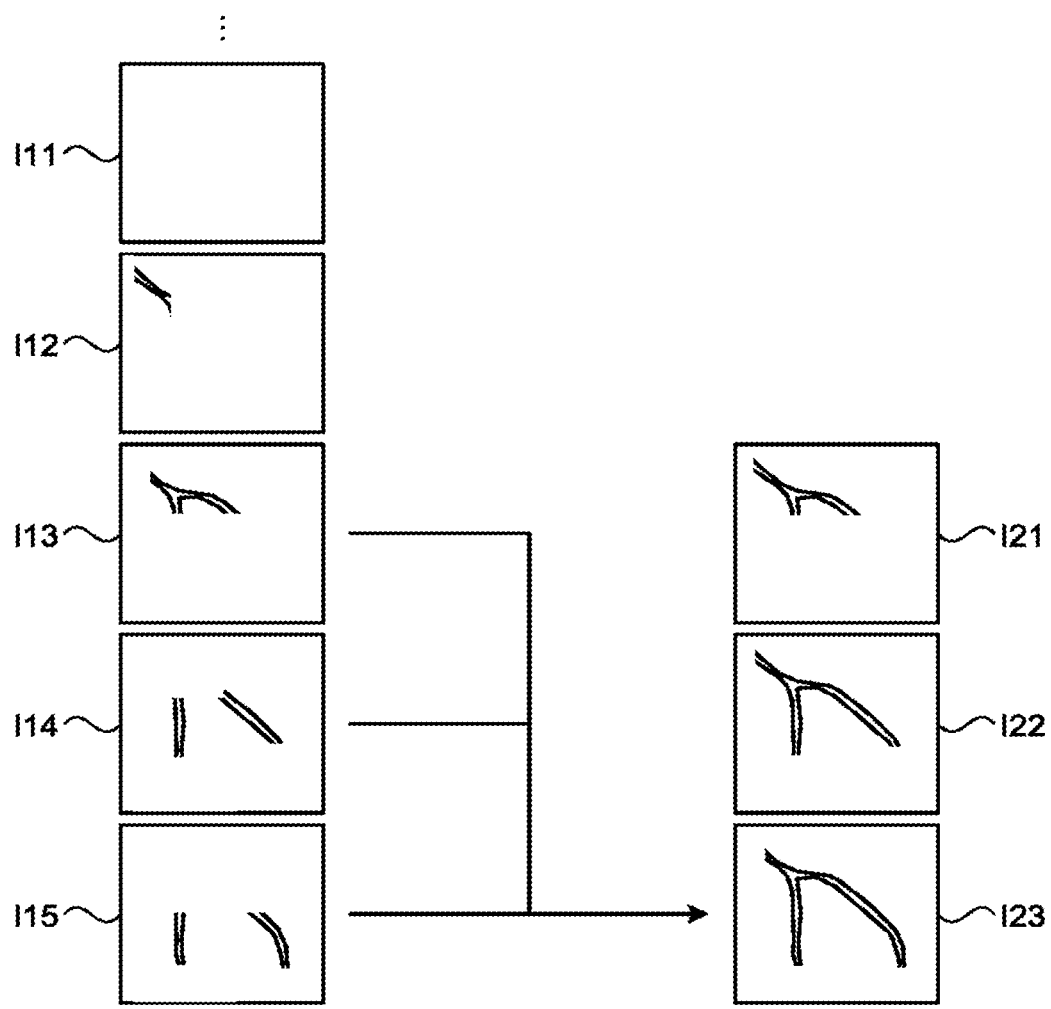
FIG. 3C is a drawing illustrating yet another example of the image processing according to the first embodiment.

After that, when the acquiring function 112b further acquires another piece of X-ray image data I15 illustrated in FIG. 3C, the acquiring function 34a acquires and stores, into the memory 33, the piece of X-ray image data I15. FIG. 3C is a drawing illustrating yet another example of the image processing according to the first embodiment. In FIG. 3C, the piece of X-ray image data I15 is X-ray image data in which the subject F is rendered while having the contrast agent injected in the blood vessels.

Subsequently, the generating function 34c generates a largest value image for each of the groups made up of pieces of X-ray image data that correspond to the number of frames "3 frames" set by the setting function 34b and are among the plurality of pieces of X-ray image data acquired by the acquiring function 34a. For example, as illustrated in FIG. 3C, the generating function 34c generates a largest value image I23 with respect to the pieces of X-ray image data in the "3 frames" including the new piece of X-ray image data I15 and the pieces of X-ray image data I13 and I14 acquired immediately before the piece of X-ray image data I15.

After that, the display controlling function 34d causes the display 32 to display the largest value image I23 generated by the generating function 34c. For example, the display controlling function 34d switches the display of the largest value image I22 that has been displayed on the display 32 into display of the largest value image I23. In this situation, as illustrated in FIG. 3C, when compared with the largest value image I22, the largest value image I23 renders the carbon dioxide that has diffused farther downstream. Accordingly, by having the largest value images I21, I22, and I23 displayed, the operator is able to visually recognize not only the shapes of the blood vessels, but also the manner in which the contrast agent diffuses in the blood vessels.

Further, the memory 33 stores therein the largest value image I23 generated by the generating function 34c. Alternatively, the generating function 34c may output the generated largest value image I23 to the image storing apparatus 20. In that situation, the image storing apparatus 20 stores therein the largest value image I23 generated by the generating function 34c. After generating the largest value image I23, the generating function 34c may delete the piece of X-ray image data I13 stored in the memory 33.

Figure 3D:
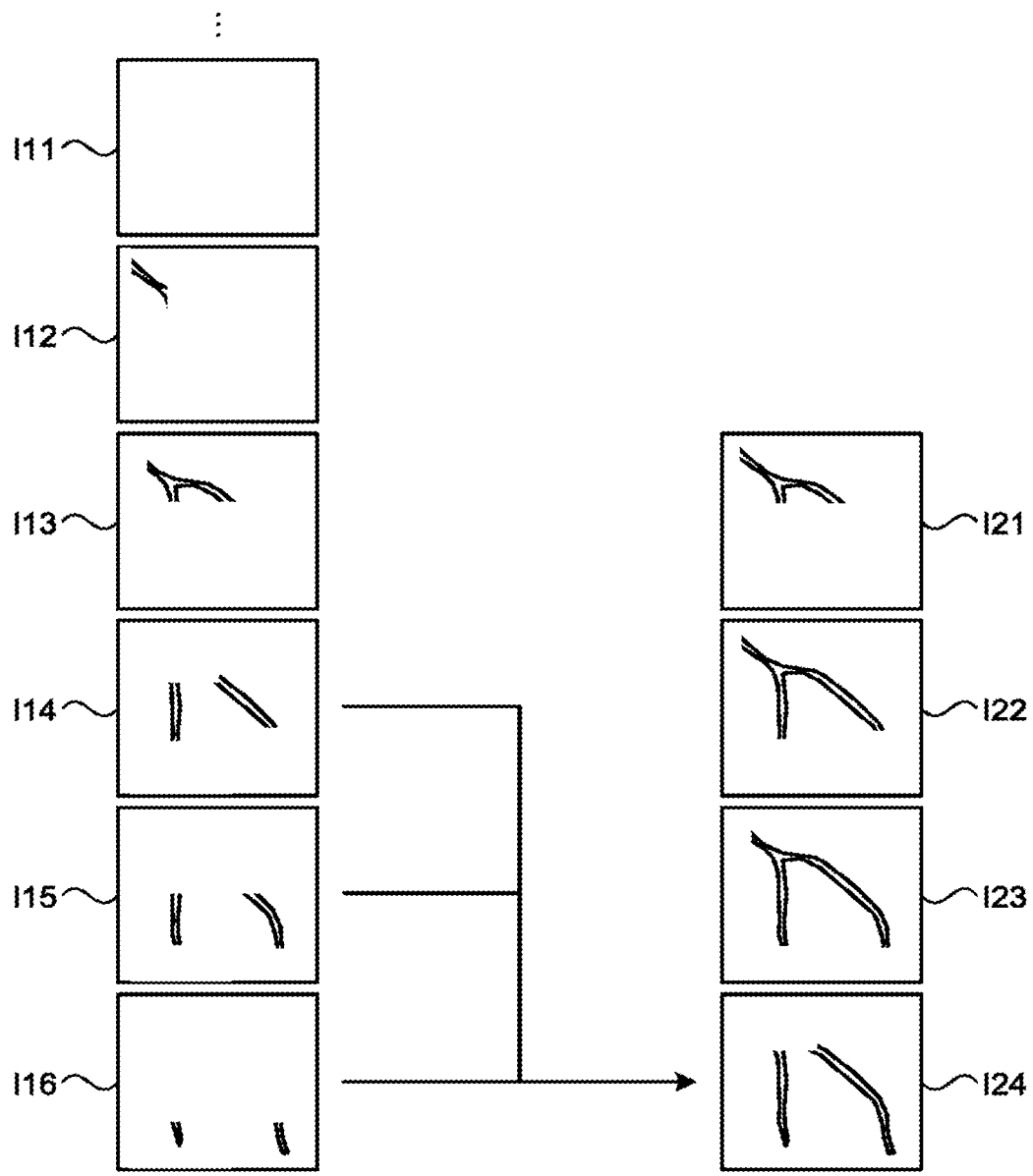
FIG. 3D is a drawing illustrating yet another example of the image processing according to the first embodiment.

After that, when the acquiring function 112b further acquires yet another piece of X-ray image data I16 illustrated in FIG. 3D, the acquiring function 34a acquires and stores, into the memory 33, the piece of X-ray image data I16. FIG. 3D is a drawing illustrating yet another example of the image processing according to the first embodiment. In FIG. 3D, the piece of X-ray image data I16 is X-ray image data in which the subject P is rendered while having the contrast agent injected in the blood vessels.

Subsequently, the generating function 34c generates a largest value image for each of the groups made up of pieces of X-ray image data that correspond to the number of frames "3 frames" set by the setting function 34b, and are among the plurality of pieces of X-ray image data acquired by the acquiring function 34a. For example, as illustrated in FIG. 3D, the generating function 34c generates a largest value image I24 with respect to the pieces of X-ray image data in the "3 frames" including the new piece of X-ray image data I16 and the pieces of X-ray image data I14 and I15 acquired immediately before the piece of X-ray image data I16.

After that, the display controlling function 34d causes the display 32 to display the largest value image I24 generated by the generating function 34c. For example, the display controlling function 34d switches the display of the largest value image I23 that has been displayed on the display 32 into display of the largest value image I24. In this situation, as illustrated in FIG. 3D, when compared with the largest value image I23, the largest value image I24 has a region in which no carbon dioxide is rendered in such a part of the blood vessel that is positioned upstream. This region is a region into which the carbon dioxide had flowed in and from which substantially all of the carbon dioxide subsequently flowed out along with the blood flow. Accordingly, by having the largest value images I21, I22, I23, and I24 displayed, the operator is able to visually recognize not only the shapes of the blood vessels, but also the manner in which the contrast agent flows, from the time when the contrast agent flows into the blood vessels, to the time when the contrast agent flows out.

Further, the memory 33 stores therein the largest value image I24 generated by the generating function 34c. Alternatively, the generating function 34c may output the generated largest value image I24 to the image storing apparatus 20. In that situation, the image storing apparatus 20 stores therein the largest value image I24 generated by the generating function 34c. After generating the largest value image I24, the generating function 34c may delete the piece of X-ray image data I14 stored in the memory 33.

As explained above, the acquiring function 34a is configured to sequentially acquire the pieces of X-ray image data acquired by the X-ray diagnosis apparatus 10. Further, the generating function 34c is configured to sequentially generate the largest value images, for the groups each being made up of pieces of X-ray image data corresponding to "3 frames" and each including a newly-acquired piece of X-ray image data and the two pieces of X-ray image data acquired immediately before the newly-acquired piece of X-ray image data. In other words, the generating function 34c is configured to generate the largest value images in parallel with at least one selected from between the acquisition of the pieces of X-ray image data performed by the X-ray diagnosis apparatus 10 and the acquisition of the pieces of X-ray image data performed by the acquiring function 34a.

The example in which the contrast agent is carbon dioxide as been explained above; however, the contrast agent may be a gaseous contrast agent other than carbon dioxide such as oxygen, nitrogen, air, or the like or may be a contrast agent of which the main component is iodine, barium sulfate, or the like. For example, when the contrast agent is a contrast agent of which the main component is iodine (hereinafter, simply "iodine"), the generating function 34c generates a smallest value image for each of the groups made up of pieces of X-ray image data corresponding to the set number of frames. In contrast, for example, when the contrast agent is a gaseous contrast agent, the generating function 34c generates a largest value image for each of groups made up of pieces of X-ray image data corresponding to the set number of frames. Further, when there is no particular restriction about the type or the amount of the contrast agent to be used, the generating function 34c does not necessarily have to generate the largest value images or the smallest value images. For example, when the contrast agent is iodine, while there is no particular restriction about the amount to be used, the display controlling function 34d causes the display to display X-ray images acquired by the acquiring function 34a.

Next, an example of a procedure in processes performed by the medical image processing apparatus 30 will be explained with reference to FIG. 4. FIG. 4 is a flowchart for explaining a flow in a series of processes performed by the medical image processing apparatus 30 according to the first embodiment. Steps S104 and S109 are steps corresponding to the acquiring function 34a. Steps S101, S102, and S103 are steps corresponding to the setting function 34b. Steps S105, S106, and S107 are steps corresponding to the generating function 34c. Step S108 is a step corresponding to the display controlling function 34d.

At first, the processing circuitry 34 judges whether or not an input operation indicating the number of frames has been received (step S101). When an input operation indicating the number of frames has been received (step Yes), the processing circuitry 34 sets the input number of frames (step S102). On the contrary, when no input operation indicating the number of frames has been received (step S101: No), the processing circuitry 34 sets a pre-set value as the number of frames (step S103).

Subsequently, the processing circuitry 34 acquires a plurality of pieces of X-ray image data in a time series (104) and judges whether or not the contrast agent is a gaseous contrast agent (step S105). When the contrast agent is a gaseous contrast agent (step S105: Yes), the processing circuitry 34 generates a largest value image for each of the groups made up of pieces of X-ray image data corresponding to the set number of frames (step S106). On the contrary, when the contrast agent is not a gaseous contrast agent (step S105: No), the processing circuitry 34 generates a smallest value image for each of the groups made up of pieces of X-ray image data corresponding to the set number of frames (step S107). After that, the processing circuitry 34 causes the display 32 to display the images generated at either step S106 or step S107 (step S108).

In this situation, the processing circuitry 34 judges whether or not a new piece of X-ray image data is acquired (step S109). When a new piece of X-ray image data is acquired (step S109: the processing circuitry 34 returns to step S105. On the contrary, when no new piece of X-ray image data is acquired (step S109: No), the processing circuitry 34 ends the process.

As explained above, according to the first embodiment, the acquiring function 34a is configured to acquire the plurality of pieces of X-ray image data in the time series. Further, the setting function 34b is configured to set the number of frames used as a unit during the image processing that is to be performed for each of the groups made up of pieces of X-ray image data in two or more frames. Further, for each of the groups made up of pieces of X-ray image data that correspond to the set number of frames and are among the plurality of pieces of X-ray image data, the generating function 34c is configured to generate a piece of image data in which the pixel value of each of the pixels expresses either the largest pixel value or the smallest pixel value among the corresponding pixels in the pieces of X-ray image data corresponding to the set number of frames. With these arrangements, the medical image processing apparatus 30 according to the first embodiment is able to improve the visibility of the X-ray images.

For example, although it is easier for medical doctors to see X-ray image data acquired by using a contrast agent of a type and in an amount that are normally used, there may be restrictions, in some situations, about the amount or the type of the contrast agent to be used. For example, when there is a restriction about using iodine, which is normally used, carbon dioxide may be used as an alternative. However, carbon dioxide is different from iodine for having a possibility of being separated in blood vessels and for having a tendency to have lower image contrast. In other words, for medical doctors who normally use iodine, X-ray images acquired by using carbon dioxide may be difficult to see. In those situations, by generating the largest value images from the pieces of X-ray image data acquired by using carbon dioxide, the medical image processing apparatus 30 is able to improve the visibility by complementing the separation of the contrast agent in the blood vessels and emphasizing the contrast.

Further, for example, when there is a restriction about the amount of iodine to be used, X-ray image data is acquired by using iodine in an amount smaller than normal. In that situation, by generating the smallest value images from the X-ray image data acquired by using the smaller amount of iodine, the medical image processing apparatus 30 is able to improve the visibility by emphasizing the contrast.

In the first embodiment described above, the example is explained in which the number of frames used as a unit during the image processing is set by receiving the input operation indicating the number of frames. In contrast, as a second embodiment, an example will be explained in which the number of frames is set on the basis of a frame time period (hereinafter, "frame period") and a framerate.

The medical image processing apparatus 30 according to the second embodiment has a configuration similar to that of the medical image processing apparatus 30 illustrated in FIG. 1, while a part of the processes performed by the setting function 34b is different. Thus, some of the constituent elements that are the same as those explained in the first embodiment will be referred to by using the same reference characters as those in FIG. 1, and explanations thereof will be omitted.

First, the setting function 34b is configured to set a frame period. In this situation, similarly to the number of frames, the frame period is a time period used as a unit during image processing. In other words, the generating function 34c performs the image processing for each of the groups made up of pieces of X-ray image data within the set frame period. The setting function 34b may set the frame period by receiving an input operation indicating the frame period or may set the frame period to a pre-set value. In the following sections, an example will be explained in which the frame period is set to "2 seconds".

Further, the setting function 34b acquires a framerate. In this situation, the framerate denotes the number of pieces of X-ray image data acquired per unit time period. For example, the setting function 34b acquires an X-ray radiation rate (the number of times the X-ray pulse is radiated per unit time period), as the framerate. In this situation, the setting function 34b may set the X-ray radiation rate by receiving an input operation from the operator, may acquire the X-ray radiation rate from image taking conditions set for the subject P, or may set the X-ray radiation rate to a radiation rate pre-set value.

After that, the setting function 34b sets the number of frames on the basis of the frame period and the framerate. For example, the setting function 34b sets the number of frames by multiplying the frame period by the framerate. For example, when the framerate is "3 frames per second (fps)", the setting function 34b sets the number of frames "6 frames" by multiplying the frame period "2 seconds" by the framerate "3 fps". After that, the generating function 34c generates either a largest value image or a smallest value image for each of the groups made up of X-ray images corresponding to the number of frames "6 frames" (i.e., the frame period "2 seconds").

In this situation, the framerate may not be constant in some situations. For example, the plurality of pieces of X-ray image data in the time series acquired by the acquiring function 34a may include two or more pieces of X-ray image data acquired at a framerate of "3 fps" and two or more pieces of X-ray image data acquired at a framerate of "6 fps". In that situation, the setting function 34b sets the number of frames for each piece of X-ray image data, on the basis of the frame period "2 seconds" and the framerates.

For example, for the two or more pieces of X-ray image data acquired at the framerate "3 fps", the setting function 34b sets "6 frames" as the number of frames. In contrast, for the two or more pieces of X-ray image data acquired at the framerate "6 fps", the setting function 34b sets "12 frames" as the number of frames. In other words, the generating function 34c changes the number of frames in accordance with the framerates, while having the frame period fixed. With this arrangement, with respect to the largest value images or the smallest value images each of which is generated for a group made up of the set number of frames, it is possible to arrange the time periods expressed in the images to be equal to one another.

Figure 5:
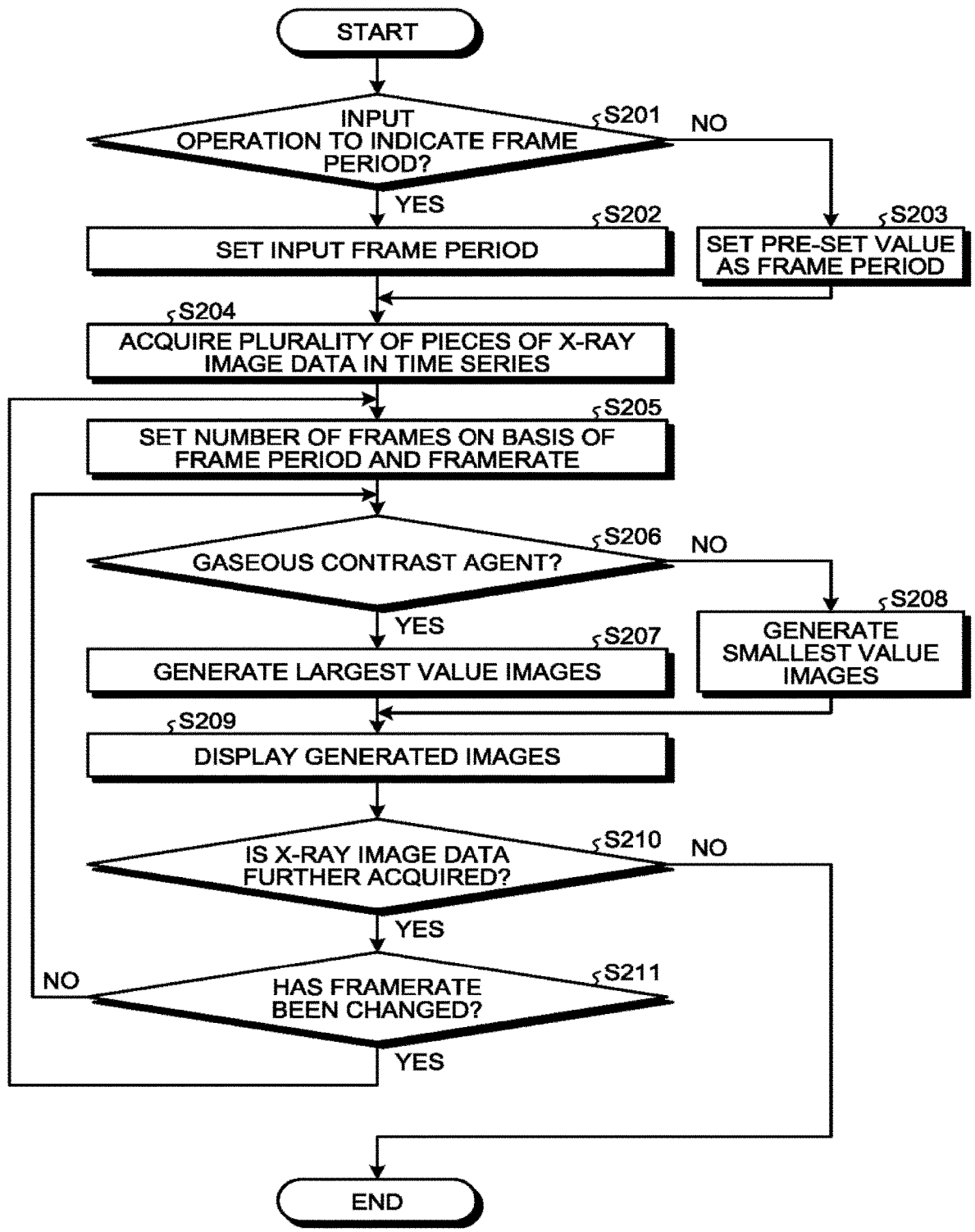
FIG. 5 is a flowchart for explaining a flow in a series of processes performed by a medical image processing apparatus according to a second embodiment.

Next, an example of a procedure in processes performed by the medical image processing apparatus 30 will be explained, with reference to FIG. 5. FIG. 5 is a flowchart for explaining a flow in a series of processes performed by the medical image processing apparatus 30 according to the second embodiment. Steps S204 and S210 are steps corresponding to the acquiring function 34a. Steps S201, S202, S203, S205, and S211 are steps corresponding to the setting function 34b. Steps S206, S207, and S208 are steps corresponding to the generating function 34c. Step S209 is a step corresponding to the display controlling function 34d.

At first, the processing circuitry 34 judges whether or not an input operation indicating a frame period has been received (step S201). When an input operation indicating a frame period has been received (step S201: Yes), the processing circuitry 34 sets the input frame period (step S202). On the contrary, when no input operation indicating a frame period has been received (step S201: No), the processing circuitry 34 sets a pre-set value as the frame period (step S203).

Subsequently, the processing circuitry 34 acquires a plurality of pieces of X-ray image data in a time series (step S204). Further, the processing circuitry 34 sets the number of frames, on the basis of the set frame period and the framerate of the acquired plurality of pieces of X-ray image data (step S205). Further, the processing circuitry 34 judges whether or not the contrast agent is a gaseous contrast agent (step S206). When the contrast agent is a gaseous contrast agent (step S206: Yes), the processing circuitry 34 generates a largest value image for each of the groups made up of pieces of X-ray image data corresponding to the set number of frames (step S207). On the contrary, when the contrast agent. Is not a gaseous contrast agent (step S206: No), the processing circuitry 34 generates a smallest value image for each of the groups made up of pieces of X-ray image data corresponding to the set number of frames (step S208). After that, the processing circuitry 34 causes the display 32 to display the images generated at either step S207 or step S208 (step S209).

In this situation, the processing circuitry 34 judges whether or not a new piece of X-ray image data is acquired (step S210). When a new piece of X-ray image data is acquired (step S210: Yes), the processing circuitry 34 judges whether or not the framerate has been changed (step S211). When the framerate has been changed (step S211: Yes), the processing circuitry 34 returns to step S205 where the processing circuitry 34 sets the number of frames, on the basis of the frame period and the post-change framerate. On the contrary, when the framerate has not been changed (step S211: No), the processing circuitry 34 returns to step S206. Further, when no new piece of X-ray image data is acquired (step S210: No), the processing circuitry 34 ends the process.

As explained above, according to the second embodiment, the setting function 34b is configured to set the frame period and to set the number of frames on the basis of the set frame period and the framerate of the plurality of pieces of X-ray image data. As a result, with respect to either the largest value images or the smallest value images each which is generated for a group made up of the set number of frames, the medical image processing apparatus 30 according to the second embodiment is able to improve the visibility by arranging the time periods expressed in the images to be equal to one another.

For example, when largest value images or smallest value images were generated by changing the frame period in accordance with the framerate while having the number of frames fixed, the span in which the contrast agent is rendered in the largest value images or the smallest value images would change, as a result of the change in the framerate. In one example, if the frame period was changed in accordance with the framerate while having the number of frames fixed, the frame period would be shortened due to an increase in the framerate, and the span in which the contrast agent is rendered in the largest value images or the smallest value images would become smaller. In contrast, because the medical image processing apparatus 30 changes the number of frames in accordance with the framerate while having the frame period fixed, it is possible, even when the framerate is changed, to prevent the span in which the contrast agent is rendered from drastically changing, in the largest value images or the smallest value images.

As a third embodiment, a variety of examples of setting the number of frames will be explained. The medical image processing apparatus 30 according to the third embodiment has a configuration similar to that of the medical image processing apparatus 30 illustrated in FIG. 1, while a part of the processes performed by the setting function 34b is different. Thus, some of the constituent elements that are the same as those explained in the first embodiment will be referred to by using the same reference characters as those in FIG. 1, and explanations thereof will be omitted.

For example, the setting function 34b may be configured to set the number of frames in accordance with the region of the subject. P rendered in the plurality of pieces of X-ray image data. For example, at first, the setting function 34b acquires information about a target region set as an image taking condition as the region of the subject P rendered in the plurality of pieces of X-ray image data. Subsequently, the setting function 34b acquires a table defining a correspondence relationship between regions and numbers of frames. The table may be, for example, generated in advance before the setting function 34b sets the number of frames and be stored in the memory 33.

For example, in the table defining the correspondence relationship between the regions and the numbers of frames, smaller numbers of frames are kept in correspondence with regions having larger movements such as the heart, whereas larger numbers of frames are kept in correspondence with regions having smaller movements. Further, by referring to the table, the setting function 34b sets the number of frames kept in correspondence with the region of the subject P rendered in the plurality of pieces of X-ray image data, as the number of frames used as a unit during the image processing. Alternatively, the table may define a correspondence relationship between regions and frame periods.

In another example, the setting function 34b may be configured to evaluate the degree of movements of the region of the subject P rendered in the plurality of pieces of X-ray image data and to set the number of frames in accordance with the evaluated degree of the movements.

For example, at first, the setting function 34b acquires two or more pieces of X-ray image data in which the subject P is rendered while having no contrast agent injected in the blood vessels, from among the plurality of pieces of X-ray image data acquired by the acquiring function 34a. In this situation, the pieces of X-ray image data in which the subject P is rendered while having no contrast agent injected in the blood vessels are, for example, pieces of X-ray image data such as the piece of X-ray image data I11 acquired before a contrast agent is injected into the subject P. Subsequently, the setting function 34b calculates, for each of the combinations made up of pieces of X-ray image data included in the acquired plurality of pieces of X-ray image data, a sum of values each acquired by squaring the difference in the pixel values between the corresponding pixels.

In this situation, among the acquired plurality of pieces of X-ray image data, there is no change in the pixel values caused by a contrast agent flowing through the blood vessels. Accordingly, the sum calculated by the setting function 34b expresses the degree of changes in the pixel values caused by movements of the region of the subject P. For this reason, by using the calculated sum values, the setting function 34b is able to evaluate the degree of the movements of the region of the subject rendered in the plurality of nieces of X-ray image data. In this situation, when more than one sum value is calculated, the setting function 34b is able to evaluate the degree of the movement a of the region of the subject P rendered in the plurality of pieces of X-ray image data, by using an average value or a mean value of the calculated sum values. Further, in accordance with the evaluated degree of the movements, the setting function 34b sets the number of frames. For example, the setting function 34b sets the number of frames in such a manner that the larger the movements are, the smaller the number of frames is.

When the movements of the region of the subject P rendered in the plurality of pieces of X-ray image data are large (e.g., when the target region is the heart), if image processing was performed while using a large number of frames as a unit, the shapes of the blood vessels rendered in the largest value images might be distorted in some situations due to the movements between the frames being reflected in the generated largest value images. In contrast, because the setting function 34b is configured to set the number of frames in accordance with the region of the subject P or to set the number of frames in accordance with the evaluated degree of the movements, it is possible to alleviate distortions of the shapes of the blood vessels rendered in the largest value images.

The first to the third embodiments have thus been explained. It is also possible to carry out the present disclosure in various different modes other than those described above in the first to the third embodiments.

In the embodiments described above, the example is explained in which the generating function 34c generates either the largest value images or the smallest value images, in parallel with at least one selected from between the acquisition of the pieces of X-ray image data performed by the X-ray diagnosis apparatus 10 and the acquisition of the pieces of X-ray image data performed by the acquiring function 34a. In other words, in the embodiments described above, the example is explained in which the generating function 34c generates either the largest value images or the smallest value images in a real-time manner. However, possible embodiments are not limited to this example.

For instance, at first, the acquiring function 34a acquires a plurality of pieces of X-ray image data in a time series including the pieces of X-ray image data I11, I12, I13, I14, I15, and I16 illustrated in FIG. 3D and stores the acquired pieces of X-ray image data into the memory 33. Further, the setting function 34b sets the number of frames used as a unit during image processing. In this situation, the setting function 34b may set the number of frames for each piece of X-ray image data. After that, the generating function 34c reads the plurality of pieces of X-ray image data from the memory 33 and further generates either a largest value image or a smallest value image for each of the groups made up of pieces of X-ray image data that correspond to the set number of frames and are among the read plurality of pieces of X-ray image data. For example, the generating function 34c reads the pieces of X-ray image data I11, I12, I13, I14, I15, and I16 from the memory 33 and further generates the largest value images I21, I22, I23, and I24, for groups each made up of pieces of X-ray image data corresponding to "3 frames".

Further, the generating function 34c may perform image processing on Digital Subtraction Angiography (DSA) image data. The DSA image data is X-ray image data generated by calculating the difference in pieces of X-ray image data between before and after the injection of a contrast agent into the subject P, so that the blood vessels of which the contrast is enhanced by the contrast agent are selectively rendered. In relation to this, a piece of X-ray image data acquired by using X-rays while a contrast agent is injected in the subject P may alternatively be referred to as a contrast image. Further, a piece of X-ray image data acquired by using X-rays while no contrast agent is injected in the subject P may alternatively be referred to as a mask image. In other words, the DSA image data is image data acquired by subtracting the mask image from the contrast image. For example, the acquiring function 34a is configured to acquire a plurality of pieces of DSA image data in a time series acquired by the acquiring function 112b. The generating function 34c is configured to generate either a largest value image or a smallest value image for each of the groups made up of pieces of DSA image data corresponding to the set number of frames.

Further, for example, the acquiring function 34a is configured to acquire the plurality of pieces of X-ray image data in the time series acquired by the acquiring function 112b. After that, the generating function 34c is configured to generate a plurality of pieces of DSA image data in a time series by subtracting a piece of X-ray image data rendering the subject P having no contrast agent injected in the blood vessels, from each of the pieces of X-ray image data which are among the plurality of pieces of X-ray image data and in which the subject P is rendered while having a contrast agent injected in the blood vessels. After that, the generating function 34c is configured to generate either a largest value image or a smallest value image for each of the groups made up of pieces of DSA image data corresponding to the set number of frames.

Further, the generating function 34c may be configured to perform an image processing on pieces of X-ray image data resulting from a motion correcting process. In this situation, the motion correcting process is, for example, a process to correct motion in the images caused by the pulsation, the respiration, body movements, and the like of the subject P. In one example, at first, the acquiring function 34a acquires a plurality of pieces of X-ray image data in a time series acquired by the acquiring function 112b. Subsequently, the generating function 34c extracts a feature point from each of the plurality of pieces of X-ray image data and further corrects motion in the pieces of X-ray image data so as to align the positions of the feature point among the images. In this situation, examples of the feature point include a marker attached to a medical device inserted in the patient and a predetermined structure of a medical device. For example, when a stent is inserted in a blood vessel of the subject P, the generating function 34c extracts, as the feature point, a marker attached to the stent, a stent strut having a mesh structure, a marker attached to a catheter or a guide wire used for inserting the stent into the blood vessel, or the like and further corrects the motion in each of the plurality of pieces of X-ray image data so as to align the positions of the feature point among the images. Further, other examples of the feature point include a structure (e.g., a bone or a soft tissue) of the subject P. In another example, the generating function 34c may correct the motion in each of the plurality of pieces of X-ray image data, in synchronization with the cycle of the pulsation or the respiration of the subject P. Further, the generating function 34c generates either a largest value image or a smallest value image for each of the groups made up of the set number of frames, on the basis of the pieces of X-ray image data resulting from the motion correcting process.

Alternatively, the acquiring function 34a may be configured to acquire a plurality of pieces of X-ray image data in a time series resulting from the motion correcting process and having been acquired by the acquiring function 112b, whereas the generating function 34c is configured to generate either a largest value image or a smallest value image for each of the groups made up of the set number of frames, on the basis of the pieces of X-ray image data resulting from the motion correcting process.

In the embodiments described above, the example is explained in which the acquiring function 34a acquires the plurality of pieces of X-ray image data in the time series from the X-ray diagnosis apparatus 10. However, possible embodiments are not limited to this example. For instance, the acquiring function 34a may acquire a plurality of pieces of X-ray image data that are transmitted from the X-ray diagnosis apparatus 10 to the image storing apparatus 20 and are stored in the image storing apparatus 20.

Further, in the embodiments described above, the example is explained in which the processing circuitry 34 in the medical image processing apparatus 30 includes the acquiring function 34a, the setting function 34b, and the generating function 34c. However, possible embodiments are not limited to this example. For instance, the processing circuitry 112 in the X-ray diagnosis apparatus 10 may include functions corresponding to the acquiring function 34a, the setting function 34b, and the generating function 34c.

Figure 6:
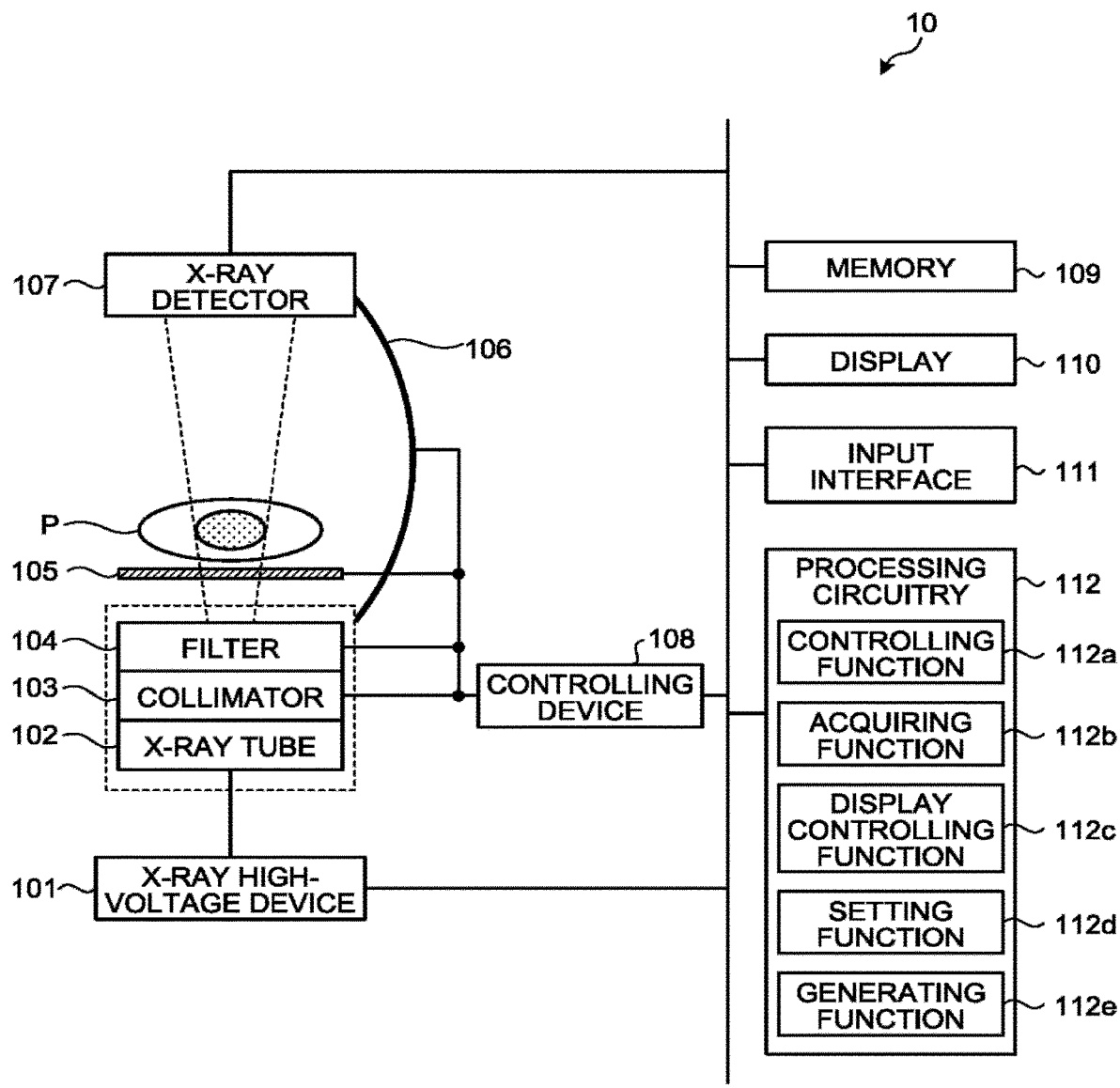
FIG. 6 is a block diagram illustrating an exemplary configuration of an X-ray diagnosis apparatus according to a fourth embodiment.

For example, the processing circuitry 112 in the X-ray diagnosis apparatus 10 may further include a setting function 112d corresponding to the setting function 34b and a generating function 112e corresponding to the generating function 34c as illustrated in FIG. 6. FIG. 6 is a block diagram illustrating an exemplary configuration of the X-ray diagnosis apparatus 10 according to a fourth embodiment.

In the example illustrated in FIG. 6, at first, the acquiring function 112b is configured to acquire a plurality of pieces of X-ray image data in a time series. Further, the setting function 112d is configured to set the number of frames used as a unit during image processing performed by the generating function 112e. Further, for each of the groups made up of pieces of X-ray image data that correspond to the number of frames set by the setting function 112d and are among the plurality of pieces of X-ray image data acquired by the acquiring function 112b, the generating function 112e is configured to generate either a largest value image or a smallest value image. After that, the display controlling function 112c is configured to cause the display 110 to display either the largest value images or the smallest value images generated by the generating function 112e.

The constituent elements of the apparatuses and the devices according to the above embodiments are based on functional concepts. Thus, it is not necessary to physically configure the constituent elements as indicated in the drawings. In other words, the specific modes of distribution and integration of the apparatuses and the devices are not limited to those illustrated in the drawings. It is acceptable to functionally or physically distribute or integrate all or a part of the apparatuses and the devices in any arbitrary unit, depending on various loads and the status of use. Further, all or an arbitrary part of the processing functions performed by the apparatuses and the devices may be realized by a CPU and a program that is analyzed and executed by the CPU or may be realized as hardware using wired logic.

Further, the medical image processing methods explained in the above embodiments may be realized by causing a computer such as a personal computer or a workstation to execute a medical image processing program prepared in advance. The medical image processing program may be distributed via a network such as the Internet. Further, the medical image processing program may be recorded on a computer-readable non-transitory recording medium such as a hard disk, a Flexible Disk (FD), a Compact Disk Read-Only Memory (CD-ROM), a Magneto-Optical (MO) disk, a Digital Versatile Disk (DVD), or the like, so as to be executed as being read from the recording medium by a computer.

According to at least one aspect of the embodiments described above, it is possible to improve the visibility of the X-ray images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising processing circuitry configured:
    to sequentially acquire X-ray images;
    to set a unit number of frames used as a unit during image processing; and
    to sequentially generate images in each of which a pixel value of each pixel expresses either a largest pixel value or a smallest pixel value among corresponding pixels in X-ray images corresponding to the unit number of frames, on a basis of the X-ray images corresponding to the unit number of frames including each of new X-ray image that is sequentially acquired and at least one X-ray image acquired before the new X-ray image.

2. The medical image processing apparatus according to claim 1, wherein the processing circuitry sets a unit time period used as a unit during the image processing and sets the unit number of frames on a basis of the unit time period and a framerate of the X-ray images.

3. The medical image processing apparatus according to claim 2, wherein the processing circuitry sets the unit time period by receiving an input operation indicating the unit time period.

4. The medical image processing apparatus according to claim 1, wherein the processing circuitry sets the unit number of frames in accordance with a region of a subject rendered in the X-ray images.

5. The medical image processing apparatus according to claim 1, wherein the processing circuitry evaluates degree of a movement of a region of a subject rendered in the X-ray images and further sets the unit number of frames in accordance with the evaluated degree of the movement.

6. The medical image processing apparatus according to claim 5, wherein the processing circuitry evaluates the degree of the movement, on a basis of the X-ray images in which the subject is rendered while having no contrast agent injected in blood vessels.

7. The medical image processing apparatus according to claim 1, wherein the processing circuitry sets the unit number of frames by receiving an input operation indicating the unit number of frames.

8. The medical image processing apparatus according to claim 1, wherein
    the processing circuitry sequentially acquires the X-ray images acquired by an X-ray diagnosis apparatus, and
    the processing circuitry sequentially generates the images in each of which the pixel value of each pixel expresses either the largest pixel value or the smallest pixel value, for groups each being made up of X-ray images corresponding to the unit number of frames and each including the new X-ray image and one or more X-ray images acquired immediately before the new X-ray image.

9. The medical image processing apparatus according to claim 1, wherein the processing circuitry acquires the X-ray images in which a subject is rendered while having a contrast agent injected in blood vessels, and in accordance with a type of the contrast agent, the processing circuitry generates one selected from between the images in each of which the pixel value of each pixel expresses the largest pixel value and the images in each of which the pixel value of each pixel expresses the smallest pixel value, for groups each made up of X-ray images corresponding to the unit number of frames.

10. The medical image processing apparatus according to claim 9, wherein the processing circuitry acquires the type of the contrast agent by receiving an input operation from an operator.

11. The medical image processing apparatus according to claim 9, wherein the processing circuitry generates, in case the contrast agent is gaseous contrast agent, the images in each of which the pixel value of each pixel expresses the largest pixel value, for groups each made up of X-ray images corresponding to the unit number of frames.

12. The medical image processing apparatus according to claim 11, wherein the processing circuitry generates, in case the contrast agent is carbon dioxide, the images in each of which the pixel value of each pixel expresses the largest pixel value, for groups each made up of X-ray images corresponding to the unit number of frames.

13. The medical image processing apparatus according to claim 1 further comprising a memory configured to store therein the images generated by the processing circuitry.

14. The medical image processing apparatus according to claim 1, wherein each of the X-ray images is an image acquired by subtracting a mask image acquired by using X-rays while no contrast agent is injected in a subject, from a contrast image acquired by using X-rays while a contrast agent is injected in the subject.

15. A medical image processing apparatus comprising:
a memory configured to store therein time series X-ray images; and
processing circuitry configured:
to set a unit number of frames used as a unit during image processing; and
to generate an image in which a pixel value of each pixel expresses either a largest pixel value or a smallest pixel value among corresponding pixels in X-ray images corresponding to the unit number of frames, while using each of a plurality of consecutive frames included in the X-ray images in the time series as a target frame, on a basis of the X-ray images corresponding to the unit number of frames including the X-ray image in the target frame that is among the time series X-ray images and at least one X-ray image acquired before the X-ray image in the target frame.

16. The medical image processing apparatus according to claim 15, wherein the processing circuitry sets a unit time period used as a unit during the image processing and sets the unit number of frames on a basis of the unit time period and a framerate of the X-ray images.

17. The medical image processing apparatus according to claim 15, wherein the processing circuitry sets the unit number of frames in accordance with a region of a subject rendered in the X-ray images.

18. The medical image processing apparatus according to claim 15, wherein the processing circuitry evaluates degree of a movement of a region of a subject rendered in the X-ray images and further sets the unit number of frames in accordance with the evaluated degree of the movement.

19. An X-ray diagnosis apparatus comprising:
an X-ray tube configured to radiate X-rays;
an X-ray detector configured to detect the X-rays radiated by the X-ray tube; and
the medical image processing apparatus according to claim 1,
wherein the processing circuitry configured:
to sequentially acquire X-ray images based on an output of the X-ray detector;
to set a unit number of frames used as a unit during image processing; and
to sequentially generate images in each of which a pixel value of each pixel expresses either a largest pixel value or a smallest pixel value among corresponding pixels in X-ray images corresponding to the unit number of frames, on a basis of the X-ray images corresponding to the unit number of frames including each of new X-ray image that are sequentially acquired and at least one X-ray image acquired before the new X-ray image.

20. An X-ray diagnosis apparatus comprising:
an X-ray tube configured to radiate X-rays;
an X-ray detector configured to detect the X-rays radiated by the X-ray tube; and
the medical image processing apparatus according to claim 15, wherein
the processing circuitry sequentially acquires X-ray images based on an output of the X-ray detector;
the memory stores therein time series X-ray images acquired by the processing circuitry; and
the processing circuitry sets a unit number of frames used as a unit during image processing, to sequentially acquire X-ray images based on an output of the X-ray detector, and generates an image in which a pixel value of each pixel expresses either a largest pixel value or a smallest pixel value among corresponding pixels in X-ray images corresponding to the unit number of frames, while using each of a plurality of consecutive frames included in the X-ray images in the time series as a target frame, on a basis of the X-ray images corresponding to the unit number of frames including the X-ray image in the target frame that is among the X-ray images in the time series and at least one X-ray image acquired before the X-ray image in the target frame.

* * * * *